US008002704B2

(12) United States Patent
Torp et al.

(10) Patent No.: US 8,002,704 B2
(45) Date of Patent: Aug. 23, 2011

(54) METHOD AND SYSTEM FOR DETERMINING CONTACT ALONG A SURFACE OF AN ULTRASOUND PROBE

(75) Inventors: Hans Garmann Torp, Trondheim (NO); Fredrik Orderud, Trondheim (NO); Lasse Lovstakken, Trondheim (NO)

(73) Assignee: General Electric Company, Schenectady, NY (US)

(*) Notice: Subject to any disclaimer, the term of this patent is extended or adjusted under 35 U.S.C. 154(b) by 1174 days.

(21) Appl. No.: 11/136,977

(22) Filed: May 25, 2005

(65) Prior Publication Data

US 2007/0010742 A1 Jan. 11, 2007

(51) Int. Cl.
*A61B 8/00* (2006.01)

(52) U.S. Cl. ........ 600/437; 600/407; 600/440; 128/916; 73/573; 73/575

(58) Field of Classification Search ........... 600/407–480
See application file for complete search history.

(56) References Cited

U.S. PATENT DOCUMENTS

| | | | | |
|---|---|---|---|---|
| 5,585,921 | A | 12/1996 | Pepper et al. | |
| 5,655,539 | A | 8/1997 | Wang et al. | |
| 5,720,286 | A * | 2/1998 | Chapelon et al. | 600/439 |
| 5,919,144 | A * | 7/1999 | Bridger et al. | 600/561 |
| 6,322,506 | B1 | 11/2001 | Nagai et al. | |
| 6,500,119 | B1 * | 12/2002 | West et al. | 600/437 |
| 6,678,545 | B2 | 1/2004 | Bucholz | |
| 6,740,518 | B1 | 5/2004 | Duong et al. | |
| 6,755,821 | B1 | 6/2004 | Fry | |
| 6,837,855 | B1 * | 1/2005 | Puech | 600/452 |
| 7,037,264 | B2 * | 5/2006 | Poland | 600/447 |
| 7,223,241 | B2 * | 5/2007 | Radulescu | 600/443 |
| 2004/0173389 | A1 * | 9/2004 | Sullivan | 178/18.04 |
| 2005/0197557 | A1 * | 9/2005 | Strommer et al. | 600/407 |
| 2006/0098533 | A1 * | 5/2006 | Hickling | 367/87 |
| 2006/0241440 | A1 * | 10/2006 | Eshel et al. | 600/439 |
| 2006/0247522 | A1 * | 11/2006 | McGee | 600/434 |
| 2007/0156048 | A1 * | 7/2007 | Panescu et al. | 600/439 |

* cited by examiner

*Primary Examiner* — Brian Casler
*Assistant Examiner* — Nasir Shahrestani
(74) *Attorney, Agent, or Firm* — Dean Small; The Small Patent Law Group

(57) ABSTRACT

A method and system for determining contact along a surface of an ultrasound probe are provided. The method includes frequency analyzing ultrasound signals received by the ultrasound probe and displaying indicators of acoustic contact of the ultrasound probe with an object based on the frequency analysis.

18 Claims, 5 Drawing Sheets

METHOD AND SYSTEM FOR DETERMINING CONTACT ALONG A SURFACE OF AN ULTRASOUND PROBE

BACKGROUND OF THE INVENTION

This invention relates generally to ultrasound probes, and more particularly, to probes for ultrasound medical imaging systems.

Ultrasound systems typically include ultrasound scanning devices, such as, ultrasound probes having different transducers that allow for performing various different ultrasound scans (e.g., different imaging of a volume or body). The ultrasound probes are typically connected to an ultrasound system for controlling the operation of the probes. The probes include a scan head having a plurality of transducer elements (e.g., piezoelectric crystals), which may be arranged in an array. The ultrasound system drives the transducer elements within the array during operation, such as, during a scan of a volume or body, which may be controlled based upon the type of scan to be performed.

Proper acoustical contact is needed to produce images of acceptable resolution when using phased array probes in ultrasound imaging. Proper acoustical contact is needed because in phased array probes a large part of the aperture of the probe is used for steering and focusing along each beam direction during image formation. A reduction of acoustical contact for portions of the probe surface will result in poor image resolution that may be observed as a smearing in the lateral direction of the image.

When using an ultrasound probe to scan a patient, improper acoustical contact may arise from different factors. For example, poor skin contact may be caused by use of an insufficient amount of contact gel, especially when the probe surface is not parallel to the skin surface. In cardiac imaging, proper probe contact with the patient skin can be hard to achieve due to the narrow acoustic window between the patient's ribs. An individual performing an ultrasound scan often must view a display screen, move the probe and adjust the probe settings to ensure good probe placement and acoustic contact for a given imaging application.

In operation, the experienced examiner may recognize the occurrence of, for example, poor lateral image resolution, and then adjust the probe position to improve image occurrence of poor lateral image resolution (e.g., adjust the probe position to improve image quality). However, this is a time consuming and often difficult process. For less experienced users, identifying these problems and performing operations to correct for the problems is even more difficult, thereby resulting in less than acceptable images (e.g., inability to perform proper diagnosis based on the image).

Additional factors may cause problems with providing proper probe placement. For example, phase aberrations due to, for example, fat/muscle layers in the body wall will typically create amplitude variations in the ultrasound wave fronts. This may further cause problems with proper placement of an ultrasound probe to obtain acceptable images because of an inability to identify the degree of amplitude variation.

BRIEF DESCRIPTION OF THE INVENTION

In one exemplary embodiment, a method for determining acoustic contact of an ultrasound probe with an object is provided. The method includes frequency analyzing ultrasound signals received by the ultrasound probe and displaying indicators of acoustic contact of the ultrasound probe with an object based on the frequency analysis.

In another exemplary embodiment, an ultrasound system is provided that includes an ultrasound probe configured to receive ultrasound signals, a processor configured to frequency analyze the received ultrasound signals and a display configured to display indicators of acoustic contact of the ultrasound probe with an object based on the frequency analysis.

DETAILED DESCRIPTION OF THE INVENTION

Various exemplary embodiments of the present invention provide methods and systems for controlling an ultrasound probe. More particularly, the various embodiments provide information (e.g., visual feedback information) to a user for use in controlling acoustic contact between an ultrasound probe and an object (e.g., patient) being examined. Exemplary embodiments of ultrasound systems and methods for controlling ultrasound probes are described in detail below. In particular, a detailed description of exemplary ultrasound systems will first be provided followed by a detailed description of various embodiments of methods and systems for controlling ultrasound probes. A technical effect of the various embodiments of the systems and methods described herein include at least one of providing a user with visual feedback information to control acoustic contact of an ultrasound probe with an object being examined.

Figure 1:
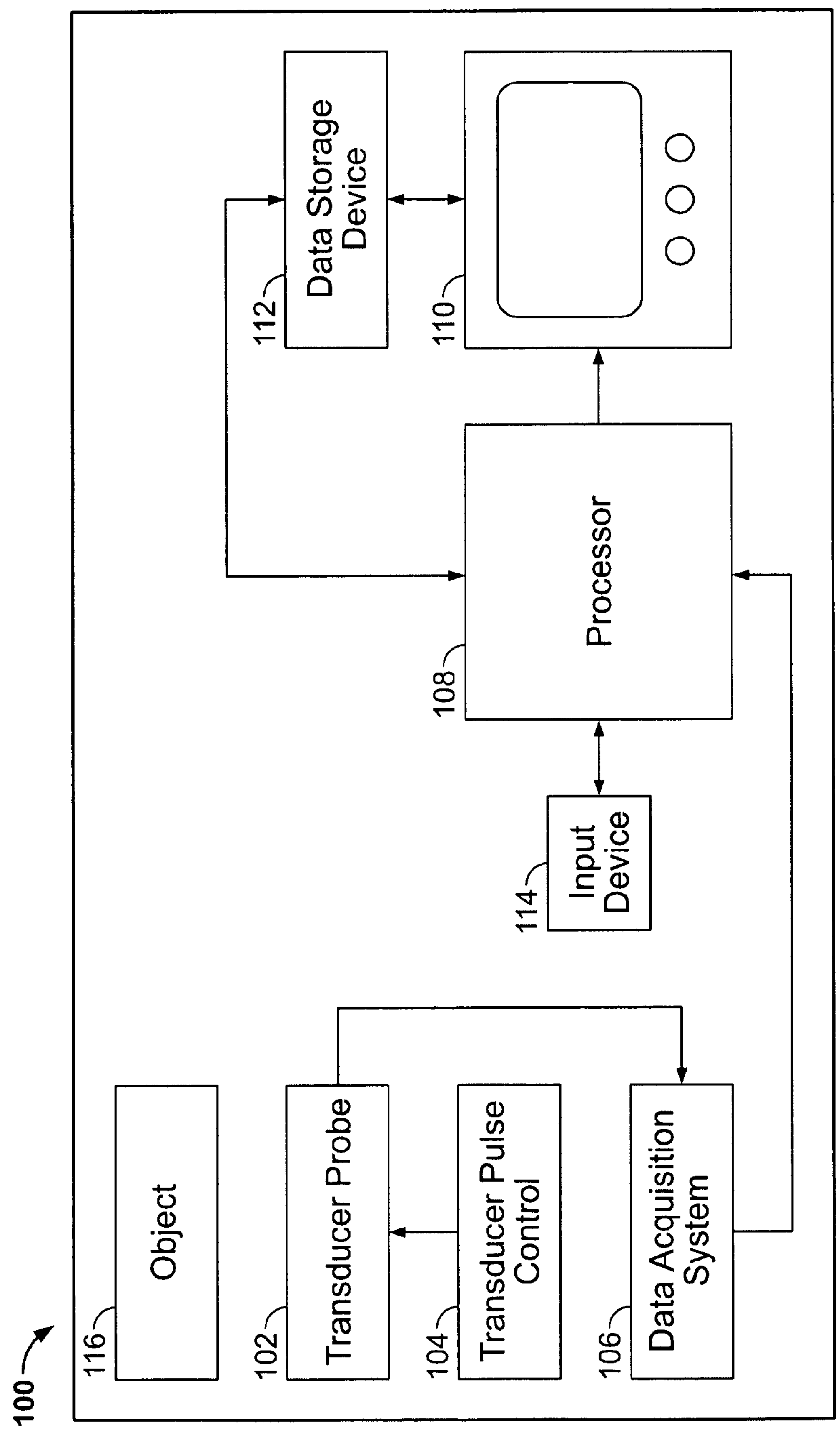
FIG. 1 is a block diagram of an ultrasound system in accordance with one exemplary embodiment of the present invention.

FIG. 1 illustrates a block diagram of an exemplary embodiment of an imaging system, and in particular, an ultrasound system 100 that may be used, for example, to acquire and process ultrasonic images. The ultrasound system 100 includes a transducer probe 102, a transducer pulse control 104, a data acquisition system (DAS) 106, a processor 108, a display unit 110, a data storage unit 112, and an input device 114. The transducer probe 102 includes at least one quartz crystal (not shown in FIG. 1). In various embodiments of the invention, the quartz crystal also may be referred to as a piezoelectric crystal. The shape of the quartz crystal changes rapidly when an electric current is applied thereto. The rapid changes in the shape of the quartz crystal and the subsequent vibrations of the quartz crystal result in emission of a plurality of ultrasound pulses. The ultrasound pulses are output at a high frequency, and the frequency of the ultrasound pulses ranges, for example, between about 1 and about 13 Megahertz (and all sub-ranges therebetween).

The ultrasound pulses are transmitted into an object 116, for example, a portion of a patient. The ultrasound pulses travel into the object 116 and hit, for example, a boundary, an obstruction, or other interface between tissues. For example, the ultrasound pulses may hit a boundary between a fluid and a soft tissue, or a boundary between the soft tissue and a bone, and so forth. The boundary may cause some of the ultrasound pulses to be reflected back while other ultrasound pulses continue to travel through the object 116 to the next boundary. In various embodiments of the invention, the ultrasound pulses that get reflected may also be referred to as echoes. The echoes are received by the transducer probe 102. The quartz crystal generates electric pulses upon receiving the echoes. In various embodiments of the invention, the quartz crystal may be simultaneously used to emit ultrasound pulses and receive the echoes. The transducer probe 102 may be moved across the surface of object 116 and angled to obtain various views of object 116.

The transducer probe 102 further may include a sound absorbing substance (not shown in FIG. 1). The sound absorbing substance eliminates the back reflections of the echoes from the transducer probe 102. Further, the transducer probe 102 includes an acoustic lens (not shown in FIG. 1) that is configured to facilitate the focusing of the transducer probe 102, for example, to focus the ultrasound pulses into the object 116. The transducer pulse control 104 is used, for example, by an ultrasonographer to set and change the frequency of the ultrasound pulses, the duration of the ultrasound pulses, and scan mode of the ultrasound system 100. The scan mode of ultrasound system refers to the mode in which the object 116 is scanned. Examples of the scan mode include, for example, A-mode, B-mode, C-mode, M-mode, and the like.

In various embodiments of the invention the transducer probe 102 includes one of a one-dimensional or two-dimensional array of piezoelectric crystals and are configured to provide phased array acquisition as is known. Further, the transducer probe 102 is configured in various embodiments to provide three-dimensional acquisition and imaging as is known. Further, and for example, the transducer probe 102 may be configured to provide two-dimensional matrix array imaging.

The DAS 106 receives the electric pulses that are generated by the quartz crystal when the quartz crystal receives the echoes. The DAS 106 digitizes the electric pulses for subsequent processing. The electric pulses that are digitized by the DAS 106 are hereinafter referred to as digitized signals. In various embodiments of the invention, the DAS 106 may be a magnetic or an optical storage media, such as, but not limited to, a hard disk, a tape drive, a compact disc (CD), and a memory chip.

The processor 108 receives the digitized signals from the DAS 106. The processor 108 further performs, for example, scan sequencing on the received digitized signals. In an exemplary embodiment of the invention, computer programs and other instructions may be uploaded into the processor 108 through the input device 114. The input device 114 is also configured to receive manual inputs from the ultrasonographer. Examples of the input device 114 include, but are not limited to, keys/buttons, audio inputs, and video input devices. The data storage unit 112 stores the ultrasound image of the object 116. In one embodiment of the invention, the data storage unit 112 also may store any intermediately processed digitized signals during the formation of the ultrasound image of the object 116. The display unit 110 displays the ultrasound image of the object 116. In various embodiments of the invention, the display unit 110 includes one of, but is not limited to, a cathode ray display, a Liquid Crystal Display (LCD), and plasma display.

Figure 2:
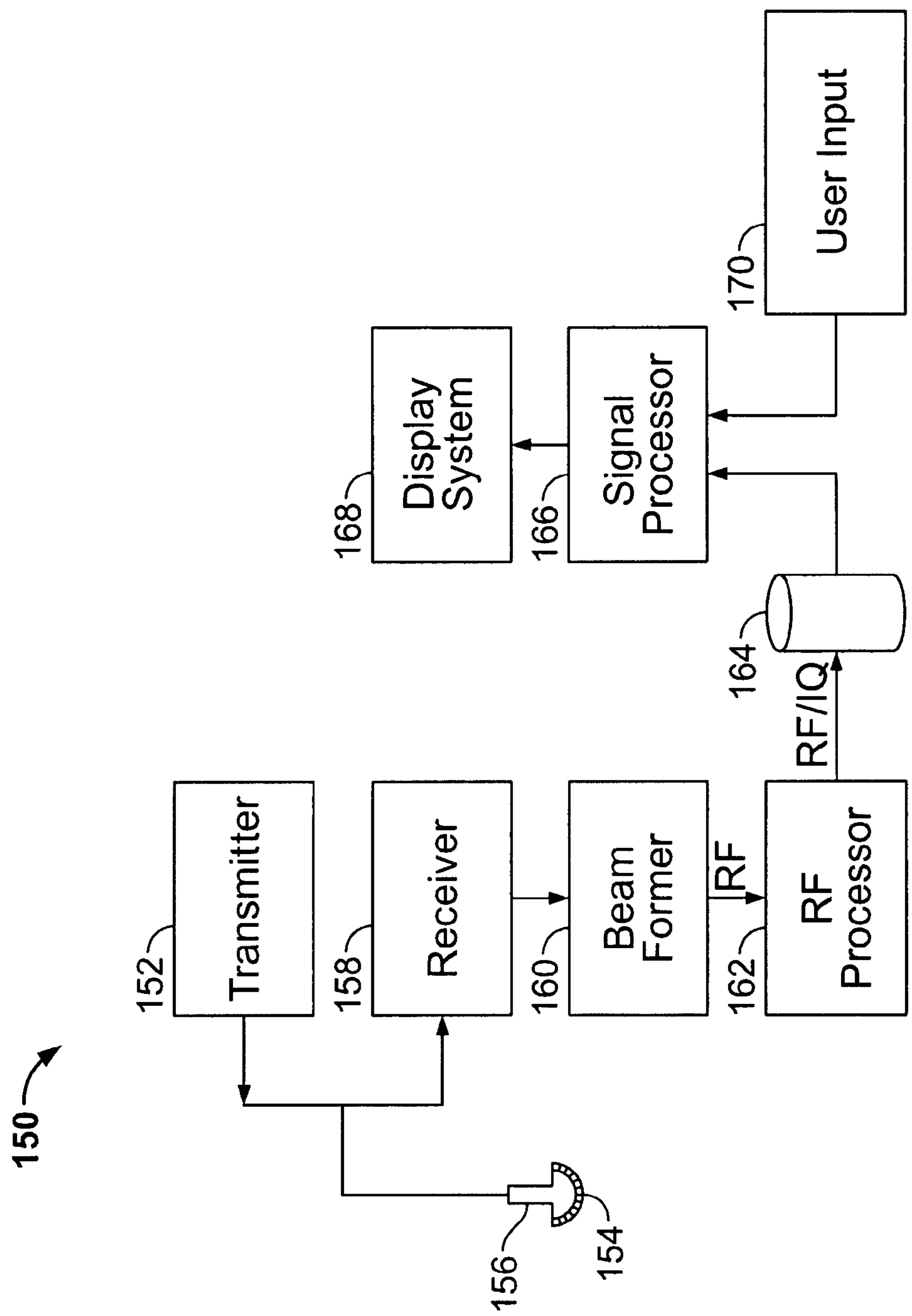
FIG. 2 is a block diagram of an ultrasound system in accordance with another exemplary embodiment of the present invention.

FIG. 2 illustrates a block diagram of another exemplary embodiment of an ultrasound system 150 that may be used, for example, to acquire and process ultrasonic images. The ultrasound system 150 includes a transmitter 152 that drives an array of elements 154 (e.g., piezoelectric crystals) within or formed as part of a transducer 156 to emit pulsed ultrasonic signals into a body or volume. A variety of geometries may be used and one or more transducers 156 may be provided as part of a probe (not shown), such as, for example, a phased array probe. The pulsed ultrasonic signals are back-scattered from density interfaces and/or structures, for example, in a body, like blood cells or muscular tissue, to produce echoes that return to the elements 154. It should be noted that the array of elements 154 may be electronically controlled, for example, by electronic switching or by electronic steering as is known. For example, in a phased array probe, the transducer 156 may be controlled to project and receive ultrasound in several directions to produce a triangular image diverging from a point of contact that may be switched or steered electronically.

The echoes are received by a receiver 158 and provided to a beamformer 160. The beamformer performs beamforming on the received echoes and outputs an RF signal. The RF signal is then processed by an RF processor 162. The RF processor 162 may include a complex demodulator (not shown) that demodulates the RF signal to form IQ data pairs representative of the echo signals. The RF or IQ signal data then may be routed directly to an RF/IQ buffer 164 for storage (e.g., temporary storage).

The ultrasound system 150 also includes a signal processor 166 to process the acquired ultrasound information (i.e., RF signal data or IQ data pairs) and prepare frames of ultrasound information for display on a display system 168. The signal processor 166 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 164 during a scanning session and processed in less than real-time in a live or off-line operation.

It should be noted that the display system 168 also may display additional information for controlling the ultrasound system 150, including for example, feedback information to control the acoustic contact of a probe of the ultrasound system 150 with an object being imaged as described in more detail herein.

A user input device 170 may be used to control operation of the ultrasound system 150. The user input device 170 may be any suitable device and/or user interface for receiving user inputs to control, for example, the type of scan or type of transducer to be used in a scan.

In connection with performing imaging or scanning operations with the ultrasound system 100 or 150, various embodiments of the invention provide information to control the acoustic contact of a probe within the ultrasound system 100 and 150 with an object being examined. In general, various embodiments for controlling a probe as described below may be implemented in connection with any ultrasound system having phased array probes and access to digital scanline RF or IQ data in real-time. The various embodiments provide information for use in ultrasound imaging applications particularly where proper acoustic contact may be hard to achieve, but is not so limited, and may provide information to improve acoustic contact to achieve improved image quality for a given imaging application.

Figure 3:
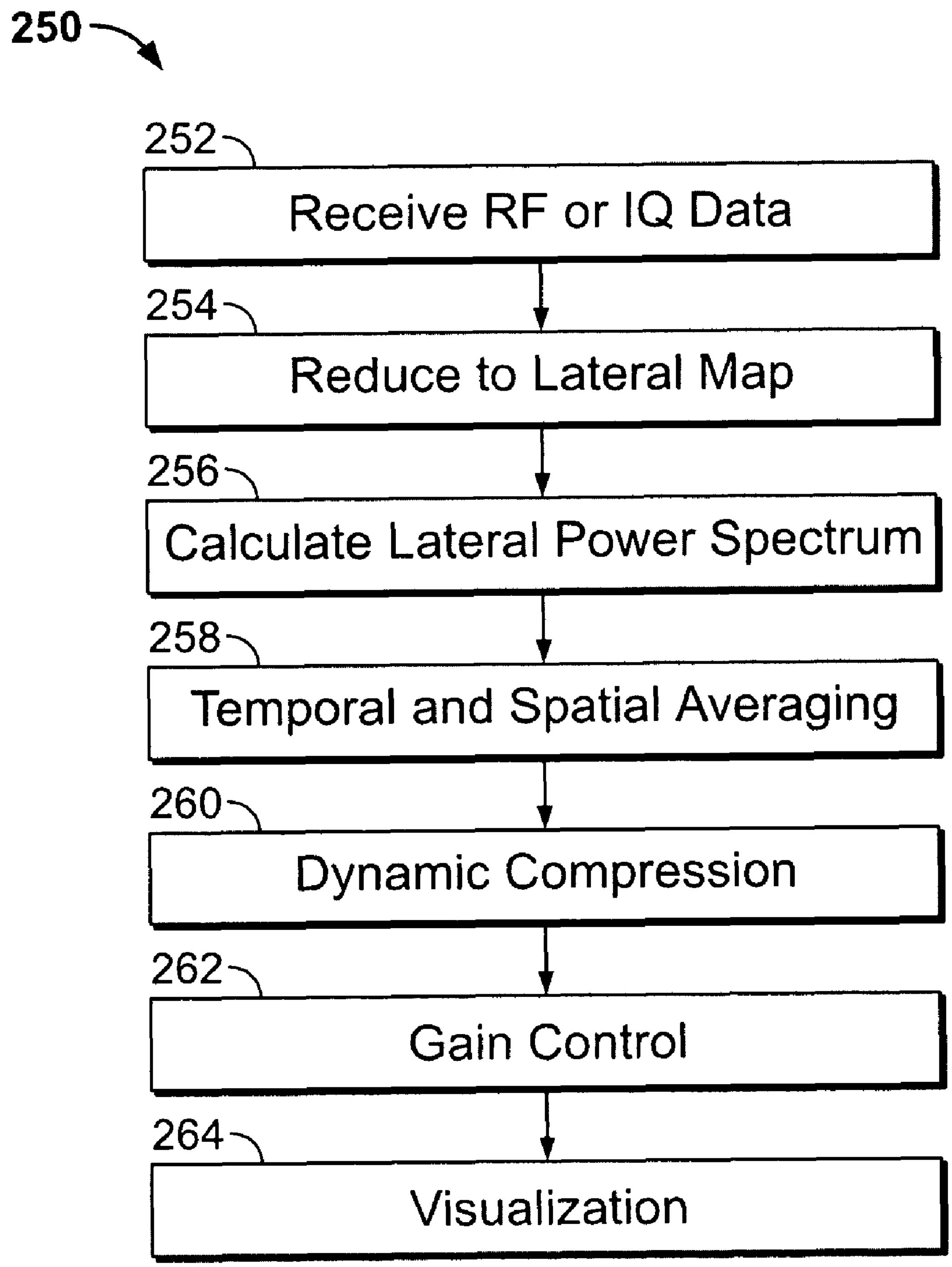
FIG. 3 is a flowchart illustrating a method for generating a visual indicator of acoustical contact along a probe scanning surface in accordance with an exemplary embodiment of the present invention.

In general, the various embodiments calculate and visualize the frequency spectrum of a received RF signal from a set of scan lines of an ultrasound image. Essentially, as described herein, the frequency spectrum is calculated and used to determine acoustic contact of a probe with an object being examined. In particular, acoustic contact along transducer apertures of a probe are calculated by frequency analyzing the received ultrasound signals. Specifically, as shown in FIG. 3, a method 250 for generating a visual indicator of acoustic contact along a probe scanning surface is provided. The method provides visual acoustic contact information to, for example, a user of an ultrasound probe to control the ultrasound probe. The method 250 includes receiving at 252 RF scanline data or complex demodulated RF scanline data from an image sector generated by, for example, the ultrasound system 100 or 150 (shown in FIGS. 1 and 2) as is known.

In operation, and for example, for a probe having a 1-D array transducer, the lateral frequency spectrum is equal to the two-way aperture function in the focal plane. This results from the Fraunhofer approximation and the assumption of linear propagation of pressure waves. Further, the two-way aperture function is given by the convolution of the transmit and receive aperture functions. A typical example of equal size transmit and receive apertures with rectangular apodization results in a triangular shaped amplitude-spectrum with a bandwidth proportional to the sum of the transmit and receive aperture as described herein. In general, the spectral shape and size is given by the aperture functions.

There is ideally a one-to-one mapping between the frequency spectrum and the autoconvolution of the probe aperture function. Comparing the Fourier transformed data to the two-way probe aperture function is performed and identifies regions with reduced spectral amplitude that correspond to regions on the aperture with improper contact. It should be noted that the various embodiments described herein may be implemented in different types of phased array probes, including, for example, probes having 2-D arrays, wherein the frequency spectrum in both the azimuth and elevation direction will provide an image of the two-dimensional aperture function. Additionally, the amplitude spectrum in the radial direction may be calculated and visualized. This 2-D (for 1-D arrays) or 3-D (for 2-D arrays) spectrum also has information relating to image resolution in the radial direction, showing for example, the amount of frequency dependent attenuation present at the current probe position.

Figure 4:
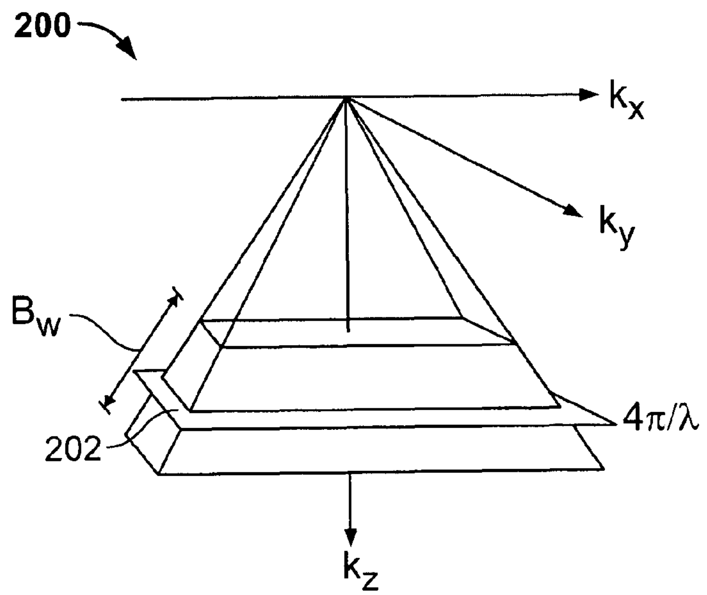
FIG. 4 is a diagram illustrating a spatial frequency response of an imaging system in accordance with various exemplary embodiments of the present invention.

Referring again to FIG. 3, thereafter at 254 the received data is processed to provide a lateral map. The lateral map is a collection of a single Fourier coefficient from a radial Fourier transform of each beam produced by the probe. More particularly, band pass filtering of the data is performed around the pulse demodulation frequency. For IQ demodulated data, this filtering simplifies to averaging (or summing) radial samples along each beam that corresponds to the low pass filtering. In operation, the more radial samples included in the summation, the narrower the filter frequency response. Specifically, and as shown in FIG. 4, a spatial frequency response 200 of the ultrasound or other imaging system is determined and which may be used to indicate image quality or acoustic contact. As shown in FIG. 4, the spatial frequency response is calculated in all three dimension in the k-space, namely $k_x$, $k_y$, and $k_z$. The spatial frequency response ($4\pi/\lambda$) of a slice 202 defining the center of central frequency is calculated as is known wherein $B_w$ defines the radial bandwidth and $\lambda$ defines the wavelength of an emitted pulse. Thus, the spectral band/plane is calculated in the k-space.

The lateral frequency spectrum is then calculated at 256 by Fourier-transforming the averaged IQ-signal. The absolute value of the spectrum is then shifted to center the zero-frequency component. Thus, the left portion of the spectrum corresponds to the left side of the probe and the right side of spectrum corresponds to the right side of the probe. It should be noted that a Fast Fourier Transform algorithm may be implemented to reduce the processing time. Further, it should be noted that various embodiments are not limited to Fourier transforming, but different processing may be performed, for example, parametric frequency spectrum analysis.

Figure 5:
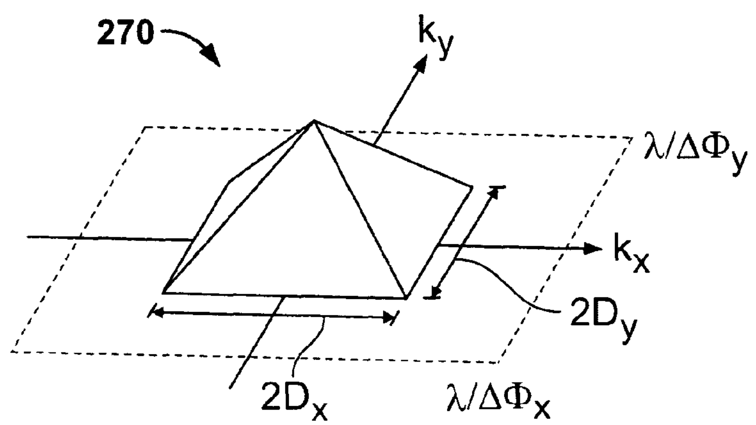
FIG. 5 is a diagram illustrating a lateral frequency response for a two-way aperture function in accordance with various exemplary embodiments of the present invention.

Referring now to FIG. 5 illustrating a lateral frequency spectrum 270 showing a triangular two-way aperture function in linear scale, assuming the probe aperture is centered around zero with a width D, then the corresponding Nyquist range is expressed as follows:

$\lambda/\Delta\Phi$, where $\Delta\Phi$ is the beam sampling density in radians and $\lambda$ is the wavelength of the transmitted pulse.

It should be noted that for second harmonic (octave) imaging, $\lambda$ is the wavelength corresponding to twice the transmitted frequency, which is shown in FIG. 5 wherein the x-axis is scaled in meters. Further, values outside D do not correspond to a part of the aperture of the probe, but are indicative of side lobes in the spectrum. If a smooth window function is used prior to the Fourier transform, the side lobes are low (e.g., −40 dB for a Hamming window). In operation, increased side lobe levels indicate the presence of unwanted signal components (e.g., reverberation noise).

Referring again to FIG. 3, temporal and spatial averaging then may be applied at 258 to reduce the variance in the spectrum estimates. For example, successive frequency spectrum images are averaged temporally from frame to frame. Spatially, each frequency spectrum is smoothed by low pass filtering. Alternatively, the available radial samples are divided into separate segments, with each producing a spectral estimate, and which are then averaged to produce one final spectrum estimate. Various known methods of frequency spectrum estimation may be used, for example, the Welch method of power spectrum estimation. Dynamic compression is then performed at 260. Specifically, in one embodiment, dynamic compression in the form of a logarithmic transform provides visualization of a range of intensities without clipping weak signals. Signal strength in ultrasound imaging may vary, for example, due to different types of tissue having varying ability to reflect ultrasound.

Gain control is then performed at 262. In operation using the ultrasound system 100 or 150, different settings and examination of different types of tissue result in different signal intensities. Gain control is used to normalize spectrum amplitude. In one embodiment, manual gain control is provided via user input device 114 (shown in FIG. 1). Specifically, a user may set the gain and dynamic range of the displayed spectrum. In other embodiments, automatic gain control may be provided using a gain control algorithm as is known.

Figure 6:
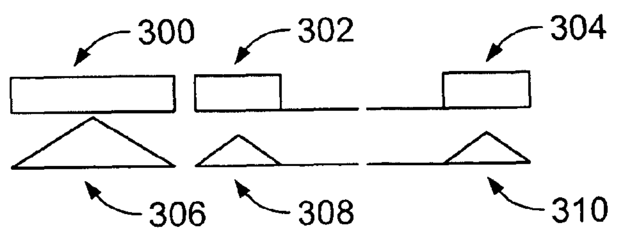
FIG. 6 is a diagram illustrating various aperture contacts and corresponding lateral spectrums for a linear phased array probe in accordance with various exemplary embodiments of the present invention.
Figure 7:
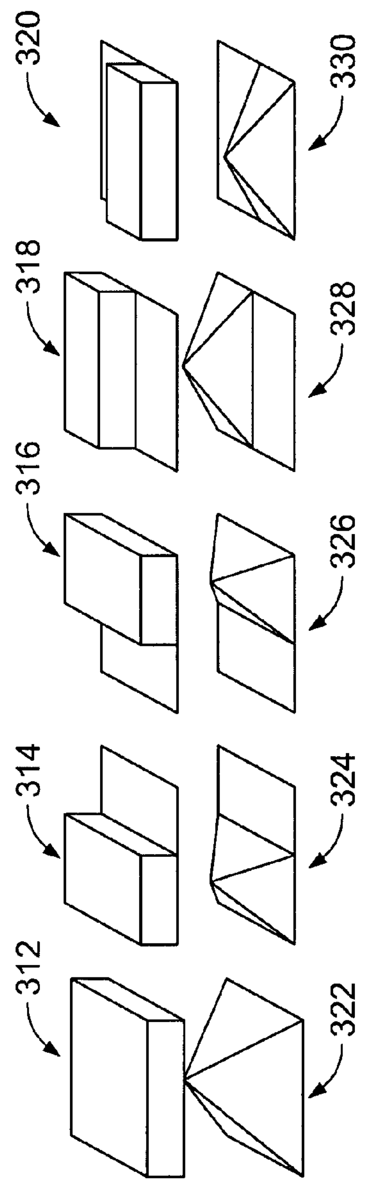
FIG. 7 is a diagram illustrating various aperture contacts and corresponding lateral spectrums for a 3D matrix probe in accordance with various exemplary embodiments of the present invention.

The lateral frequency spectrum is then visualized at 264 based on the type of probe. For example, and as shown in FIGS. 6 and 7, probes having a one-dimensional aperture generate a one-dimensional lateral spectrum that may be visualized in the form of, for example, a graph or a color-coded histogram. Probes having a two-dimensional aperture generate a two-dimensional lateral spectrum that may be visualized in the form of, for example, a color-coded two-dimensional contact map. In particular, as shown in FIG. 6, for linear phased array probes, the aperture contacts 300, 302 and 304 result in lateral spectrums 306, 308 and 310, respectively. Further, and as shown in FIG. 7, for a 3D matrix probe, the aperture contacts 312, 314, 316, 318 and 320 result in lateral spectrums 322, 324, 326, 328 and 330, respectively.

Figure 8:
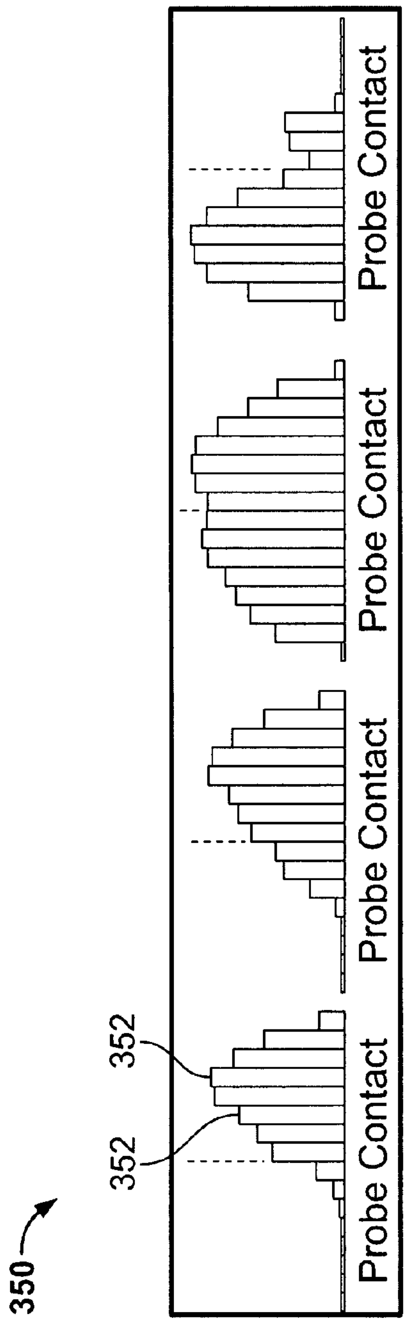
FIG. 8 is a diagram of a spectrum display having probe contact indicators in accordance with an exemplary embodiment of the present invention.

Thus, as shown in FIG. 8, a spectrum display 350 including a representation of the lateral spectrum may be generated and visualized as described herein and displayed by the ultrasound system 100 or 150 (shown in FIGS. 1 and 2), which may be displayed on, for example, display unit 110 (shown in FIG. 1) or display system 168 (shown in FIG. 2). As shown in FIG. 8, the spectrum display 350 may include a plurality of probe contact indicators 352 (e.g., color-coded bars) indicating a relative level of contact of different portions of a probe with an object being imaged (e.g., a patient). As shown in FIG. 8 from left to right, the probe gradually contacts the object from right to left as indicated by the probe contact indicators 352.

It should be noted that the method 250 may be implemented using any suitable processor or processing unit, such as, for example, the processor 108 (shown in FIG. 1) or the signal processor 166 (shown in FIG. 2).

Various modifications to the various embodiments described herein are contemplated. For example, the acoustic contact of the probe with an object may be calculated directly by measuring the signal power from individual aperture elements. Additionally, and for example, pre-beamforming may be performed, which is simpler, but needs additional hardware and processing power, and cannot be performed on prerecorded RF or IQ data. In operation, poor contact with an object results in reduced element signal power.

Thus, various embodiments of the present invention provide information to user of a probe relating to contact of the probe with an object being imaged. This information is not available from a visual inspection of the image alone, and includes, for example, the following:

1. An indication of the parts of the probe lacking sufficient contact with an object, thereby showing in which direction the probe should be moved in order to improve image quality.

2. An objective and quantitative measure of image resolution available in real-time.

A real-time visualization of change in acoustic contact is provided that improves the process of optimizing image quality by providing a user of an ultrasound probe visual feedback relating to where acoustic contact with an object is insufficient. Further, the degree of amplitude variation displayed provides a user with information to position the probe in an image plane with the least amount of aberration, thereby providing improved image quality.

While the invention has been described in terms of various specific embodiments, those skilled in the art will recognize that the invention can be practiced with modification within the spirit and scope of the claims.

What is claimed is:

1. A method for determining acoustic contact of an ultrasound probe with an object, said method comprising:

receiving radio frequency (RF) scanline data;

utilizing the RF scan line data to generate a lateral map;

calculating a lateral frequency spectrum using the lateral map;

applying at least one of a temporal and a spatial averaging filter to the lateral frequency spectrum to determine acoustic contact of the ultrasound probe with the object;

displaying indicators of acoustic contact of the ultrasound probe with an object based on the frequency analysis.

2. A method in accordance with claim 1 further comprising utilizing the RF scan line data to generate a lateral map that includes a set of Fourier coefficients derived from a radial Fourier transform of each ultrasound beam produced by the ultrasound probe.

3. A method in accordance with claim 1 further comprising performing dynamic compression to the filtered lateral frequency spectrum.

4. A method in accordance with claim 1 further comprising setting at least one of a gain and a dynamic range of the lateral frequency spectrum.

5. A method in accordance with claim 1 further comprising displaying indicators of the acoustic contact along a probe surface of the ultrasound probe contacting the object.

6. A method in accordance with claim 1 further comprising displaying indicators representative of energy levels along a probe surface of the ultrasound probe contacting the object.

7. A method in accordance with claim 5 further comprising configuring the indicators to indicate a direction to move the ultrasound probe for increased acoustic contact.

8. A method in accordance with claim 5 further comprising configuring the indicators based on a type of the ultrasound probe.

9. A method in accordance with claim 5 wherein the indicators comprise color coded elements forming one of a color-coded histogram and a color-coded contact map.

10. A method in accordance with claim 5 further comprising updating the indicators based on movement of the ultrasound probe along the object.

11. A method in accordance with claim 5 wherein the indicators are representative of image quality.

12. An ultrasound system comprising:

an ultrasound probe configured to generate radio frequency (RF) scanline data;

a processor configured to:

receive the RF scanline data;

utilize the RF scan line data to generate a lateral map;

calculate a lateral frequency spectrum using the lateral map;

apply at least one of a temporal and a spatial averaging filter to the lateral frequency spectrum to determine acoustic contact of the ultrasound probe with the object; and a display configured to display indicators of the acoustic contact of the ultrasound probe with an object.

13. The ultrasound system of claim 12 wherein the indicators represent energy levels along a probe surface of the ultrasound probe contacting the object.

14. The ultrasound system of claim 12 wherein the indicators indicate a direction to move the ultrasound probe for increased acoustic contact.

15. The ultrasound system of claim 12 wherein the indicators are based on a type of the ultrasound probe.

16. The ultrasound system of claim 12 wherein the indicators comprise color coded elements forming one of a color-coded histogram and a color-coded contact map.

17. The ultrasound system of claim 12 wherein the indicators are updated based on movement of the ultrasound probe along the object.

18. The ultrasound system of claim 12 wherein the indicators are representative of image quality.

* * * * *